US00PP08652P

United States Patent [19]

Dehan

[11] Patent Number: Plant 8,652

[45] Date of Patent: Mar. 22, 1994

[54] GYPSOPHILA PLANT NAMED WHITE FESTIVAL

[75] Inventor: Klara Dehan, Holon, Israel

[73] Assignee: Danziger - "Dan" Flower Farm, Post Beit Dagan, Israel

[21] Appl. No.: 971,569

[22] Filed: Nov. 5, 1992

[51] Int. Cl.[5] ..... A01H 5/00

[52] U.S. Cl. ..... Plt./68.1

[58] Field of Search ..... Plt. 68.1

[56] References Cited

PUBLICATIONS

Huxley, A., et al., (Eds.) "*Gypsophila*" *The New Royal Horticultural Society Dictionary of Gardening*, vol. 4, 1992, The Stockton Press, N.Y. pp. 477–478.

*Primary Examiner*—James R. Feyrer

*Attorney, Agent, or Firm*—Foley & Lardner

[57] ABSTRACT

A new and distinct cultivar of gypsophila plant named White Festival, characterized by its semi-double flower form, shiny white flower color; compact, full growth habit; floriferous habit, long and very narrow leaves, and its continuous flowering in Israel from April to December.

1 Drawing Sheet

The present invention relates to a new and distinctive cultivar of gypsophila plant, referred to by the cultivar name White Festival.

The new cultivar was developed by the inventor in Mishmar Hashiva, Israel through controlled breeding by crossing male and female parents which are unknown at this time. Both parents were selected seedlings from the breeding of grandparents which are likewise unknown at this time. Both the parents and grandparents are proprietary lines used exclusively for breeding.

Asexual reproduction by cuttings taken by the inventor at Mishmar Hashiva, Israel in 1990 has shown that the unique features of this new gypsophila are stabilized and are reproduced true to type in successive propagations.

The following characteristics in combination distinguish the new gypsophila from other cultivated gypsophila of this type known and used in the floriculture industry:

1. Semi-double flower form.
2. Shiny white flower color.
3. Flowers are carried on relatively long sturdy stems.
4. Floriferous habit, with many flowers being in bloom and bud at one time.
5. Relatively compact and full growth habit, making the plant very desirable for outdoor use in bedding areas and pots. The new cultivar is also adaptable to greenhouse pot production.
6. In Mishmar Hashiva, Israel, the new cultivar flowers continuously from approximately April through December.
7. The leaves are very long and narrow.
8. White Festival will respond to lower levels of light for flowering. Thus, under natural outdoor light conditions, White Festival will flower earlier in the spring and very late in the fall or early winter.

The accompanying colored photographs illustrate the overall appearance of White Festival, showing the colors as true as is reasonably possible to obtain in colored reproductions of this type. The top photograph shows both foliage and flowers. The bottom photograph is similar to the top photo but shows the flowers somewhat more enlarged.

The following is a detailed description of the new cultivar based on plants produced under commercial practice in Mishmar Hashiva, Israel.

Color references are made to the Royal Horticultural Society Colour Chart (RHS) except where general terms of ordinary dictionary significance are used.

White Festival can be compared with and is similar in certain respects to the cultivar Bristol Fairy. Differences are that White Festival has shiny white flower color compared to the more greenish white flowers of Bristol Fairy; more branches, and White Festival will flower better in reduced natural light conditions.

Parentage: Both male and female parents are unknown.

Propagation: By tip cuttings; rooting is excellent.

Plant description:

A. *Form.*—Compact, mounded.

B. *Habit of growth.*—Strong, plant is fully rounded and reaches 50 cm in maximum height (including flowers) at time of full and continuous flowering in spring and summer; diameter of plant tends to increase under reduced light or short day conditions when shoot formation tends to increase. An increase in shoots tends to increase overall diameter at time of flowering. The plant is a perennial in Israel, where minimum average winter temperatures are approximately 10° C. Plants of White Festival have survived freezing temperatures as low as −2° to −6° C.

C. *Foliage.*—1. Size: Very long and narrow; when fully grown, leaves are approximately 12 cm in length and 1.3 cm in width; immature leaves are 4 cm long and 0.5 cm wide. 2. Shape: Linear. 3. Margin: Smooth. 4. Color: Top side: 137B. Underside: 137C.

Flowering description:

A. *Natural flowering season.*—In Israel under outdoor conditions, flowering starts in April and continues until December.

B. *Flower buds.*—Closed bud is oval to spherical, being approximately 2 mm both in height and in width; just before opening (when color can be seen), bud is generally oval, 3 mm tall and 2 mm in width.

C. *Flowers borne.*—On relatively long, strong stems out of leaf whorl.

D. *Quantity of flowers.*—Very floriferous.

E. *Petals.*—1. Shape: Generally round. 2. Color: 155B. 3. Number of petals: Approximately 25, and up to 30. 4. Size of flowers: 0.7 to 0.8 cm in total flower diameter.

F. *Reproductive organs.*—Flowers are monoecious. 1. Stamen: 3–5 anthers, very thin, approximately 0.2 to 0.3 mm in diameter and 3–5 mm long; pollen is white. 2. Pistil: Stigma 4 mm in length and 0.2 to 0.3 mm in diameter, white in color; style is green and 1 mm in diameter and length.

G. *Disease resistance.*—Festival has not been shown to be sensitive to botrytis or other common diseases.

I claim:

1. A new and distinct cultivar of gypsophila plant named White Festival, as illustrated and described.

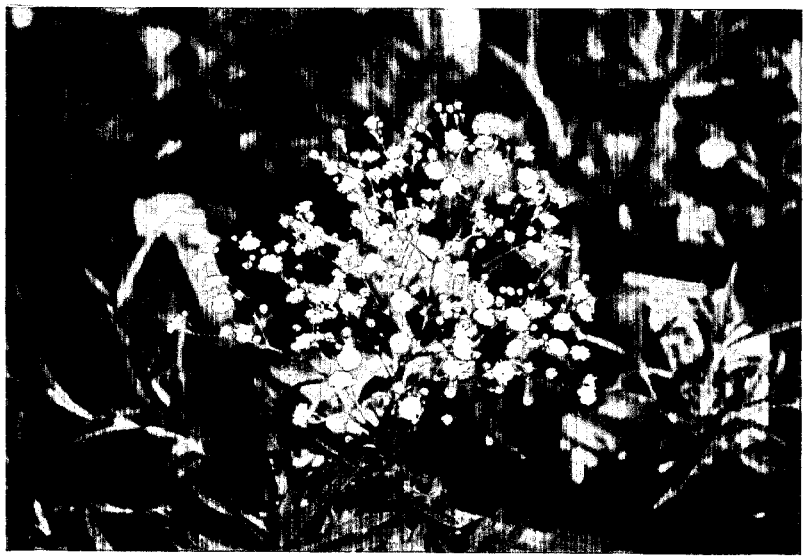
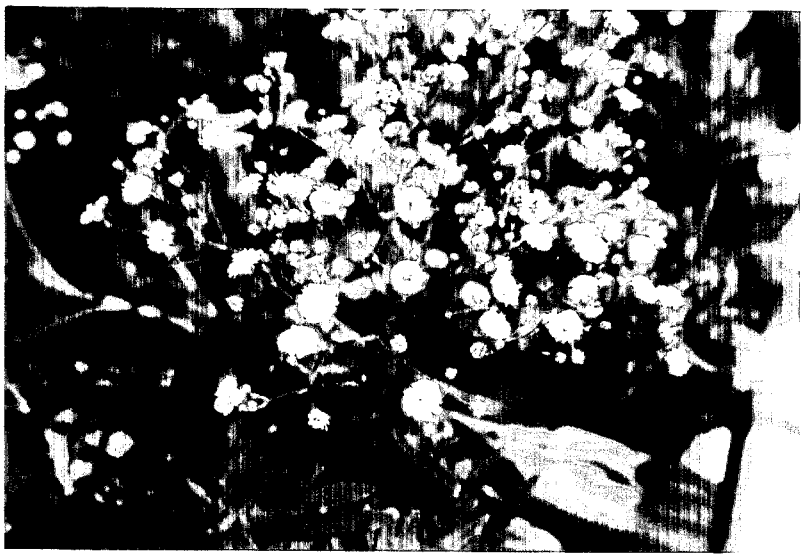

* * * * *